(12) United States Patent
Johnson et al.

(10) Patent No.: US 10,470,426 B1
(45) Date of Patent: Nov. 12, 2019

(54) ALFALFA VARIETY CW 104014

(71) Applicant: Alforex Seeds LLC, Indianapolis, IN (US)

(72) Inventors: David W. Johnson, La Crosse, WI (US); Mark E. Darling, Lansing, IA (US); Tracy A. Engh, Westby, WI (US)

(73) Assignee: Alforex Seeds LLC, Indianapolis, IN (US)

( * ) Notice: Subject to any disclaimer, the term of this patent is extended or adjusted under 35 U.S.C. 154(b) by 0 days.

(21) Appl. No.: 16/201,031

(22) Filed: Nov. 27, 2018

Related U.S. Application Data

(60) Provisional application No. 62/592,052, filed on Nov. 29, 2017.

(51) Int. Cl.
*A01H 6/54* (2018.01)
*A01H 5/10* (2018.01)

(52) U.S. Cl.
CPC .............. *A01H 6/544* (2018.05); *A01H 5/10* (2013.01)

(58) Field of Classification Search
None
See application file for complete search history.

(56) References Cited

U.S. PATENT DOCUMENTS

2006/0206969 A1* 9/2006 Johnson ............ A01H 5/10 800/295

OTHER PUBLICATIONS

AOSCA application for variety CW 104014, dated Nov. 30, 2017.
AOSCA application for variety SolarGold, dated Nov. 30, 2017.

* cited by examiner

*Primary Examiner* — Vinod Kumar

(57) ABSTRACT

The present disclosure relates to the seeds, plants and plant parts thereof of alfalfa variety CW 104014, and to methods for producing progeny of alfalfa variety CW 104014 by crossing alfalfa variety CW 104014 with another alfalfa plant. The disclosure also relates to methods for producing an alfalfa plant derivative of alfalfa variety CW 104014, containing in its genetic material one or more transgenes introduced into alfalfa variety CW 104014, and to the transgenic alfalfa plants and plant parts produced by those methods. The disclosure also relates to alfalfa varieties or breeding varieties, and plant parts derived from alfalfa variety CW 104014.

19 Claims, No Drawings

ALFALFA VARIETY CW 104014

CROSS-REFERENCE TO RELATED APPLICATIONS

This application claims the benefit of priority to U.S. Provisional Patent Application No. 62/592,052, filed Nov. 29, 2017, the entire disclosure of which is herein incorporated by reference.

BACKGROUND

Alfalfa is grown for hay, pasture and silage, and is valued highly as a livestock feed. Alfalfa is highly effective in nitrogen fixation, and is frequently planted in crop rotation to replenish nutrients depleted from the soil by other crops such as corn. Alfalfa is an herbaceous perennial legume characterized by a deep tap root showing varying degrees of branching. The plants have erect or semi-erect stems, bearing an abundance of leaves, and grow to a height of 2-4 feet. The number of stems arising from a single woody crown may vary from just a few to 50 or more. New stems develop when older ones mature or have been cut or grazed. Flowers are borne on axillary racemes which vary greatly in size and number of flowers. Flower color is predominantly purple, or bluish-purple, but other colors occur. The fruit is a legume, or pod, usually spirally coiled in *M. sativa*. Seeds are small, with about 220,000/lb., and the color varies from yellow to brown.

Alfalfa is widely adapted to temperature and soil conditions, except for humid tropical conditions. Reproduction in alfalfa is mainly by cross-fertilization, but substantial self-pollination may also occur. Cross-pollination is effected largely by bees. Two species of alfalfa, *M. sativa* and *M. falcata*, have become important forage plants with *Medicago sativa* L. (also known as lucerne) being one of the world's most valuable forage legumes.

Increasing alfalfa fiber digestibility by decreasing lignin content is known to improve forage quality, ration formulation flexibility, and enhance feed value. Doing so while not adversely affecting yield and without having to introduce transgenes to develop stable, high yielding varieties with low or reduced lignin content has long been a goal of alfalfa breeders. U.S. Pat. No. 9,648,826 discloses one variety having reduced lignin content. However, additional alfalfa varieties are desired that have reduced Acid Detergent Lignin (ADL) content compared to known alfalfa varieties.

The commercial production of seeds for growing alfalfa plants normally involves four stages, the production of breeder, foundation, certified and registered seeds. Breeder seed is the initial increase of seed of the strain which is developed by the breeder and from which foundation seed is derived. Foundation seed is the second generation of seed increase and from which certified seed is derived. Certified seeds are used in commercial crop production and are produced from foundation or certified seed.

SUMMARY

The present disclosure relates to a new alfalfa variety wherein said plants have reduced Acid Detergent Lignin (ADL) content compared to a control alfalfa variety grown under the same field growing conditions. More particularly, in one embodiment a new alfalfa variety is provided that exhibits low Acid Detergent Lignin (ADL), high forage dry matter yield, high forage milk per acre using Milk 2000, and/or high forage NDFD.

In one embodiment of the present disclosure, there is provided a novel alfalfa variety, designated CW 104014. More particularly, one aspect of the present disclosure relates to seed of alfalfa variety CW 104014, to the plants of alfalfa variety CW 104014, and the plant parts of alfalfa variety CW 104014. The present disclosure also provides a method for making an alfalfa plant derived from alfalfa variety CW 104014, wherein the method comprises crossing alfalfa variety CW 104014 with another alfalfa plant. In one embodiment the present disclosure also relates to methods for making an alfalfa plant that comprises in its genetic material one or more traits introgressed into CW 104014 through backcross conversion and/or transformation, and to the alfalfa seed, plant and plant parts produced by such methods. The present disclosure further relates to alfalfa seed, plant or plant parts produced by crossing the alfalfa variety CW 104014 (or a derivative of CW 104014 modified to comprise one or more additional traits) with another alfalfa variety.

In one embodiment the present disclosure is directed to seed of alfalfa variety CW 104014, representative seed having been deposited under ATCC Accession Number PTA-124567. The present disclosure is also directed to a seed of said alfalfa variety or regenerable parts of said seed. The present disclosure is also directed to a plant, or a part thereof (including pollen, ovule or seed), produced by growing seed of alfalfa variety CW 104014 as well as F1 progeny of a plant grown from the seed of alfalfa variety CW 104014, wherein the F1 progeny having retained the low ADL levels of alfalfa variety CW 104014 and/or all the physiological and morphological characteristics of alfalfa variety CW 104014.

The present disclosure is also directed to a tissue culture of regenerable cells from an alfalfa variety CW 104014 plant, or a plant part thereof. The regenerable cells may be selected from the group consisting of protoplasts and calli, wherein the regenerable cells are from a leaf, pollen, ovule, cotyledon, hypocotyl, embryo, root, pod, flower, shoot or stalk. Protoplasts produced from said tissue culture are also encompassed by the present disclosure. The present disclosure is also directed to an alfalfa plant regenerated from said tissue culture, wherein the alfalfa plant has all of the physiological and morphological characteristics of a plant produced by growing a seed designated CW 104014 and deposited under ATCC Accession No. PTA-124567.

The present disclosure is also directed to a method for producing an alfalfa variety CW 104014-derived alfalfa plant. The method comprises: (a) crossing CW 104014 plants grown from CW 104014 seed, representative seed of which has been deposited under ATCC Accession No: PTA-124567, with a second alfalfa plant to yield progeny alfalfa seed; and (b) growing the progeny seed to yield an alfalfa variety CW 104014-derived alfalfa plant. The method may further comprise: (c) crossing the alfalfa variety CW 104014-derived alfalfa plant of (b) with itself or a third alfalfa plant to yield a second alfalfa CW 104014-derived alfalfa progeny seed; and (d) growing the second alfalfa progeny seed of (c) to yield a second alfalfa variety CW 104014-derived alfalfa a plant. Steps (c) and (d) may be repeated at least one time to generate an additional alfalfa variety CW 104014-derived alfalfa plant.

Also encompassed in the present disclosure is a method of introducing a desired trait into alfalfa CW 104014 as well as the plants and plant parts produced by such a method. The method comprises: (a) crossing CW 104014 plants grown from CW 104014 seed, representative seed of which has been deposited under ATCC Accession No: PTA-124567, with plants of a second alfalfa variety that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates; (b) selecting F1 progeny plants that have the desired trait to produce selected F1 progeny plants; (c) crossing the selected progeny plants with the CW 104014 plants to produce backcross progeny plants; (d) selecting for backcross progeny plants that have the desired trait and physiological and morphological characteristics of alfalfa variety CW 104014 to produce selected backcross progeny plants; and optionally (e) repeating steps (c) and (d) three or more times in succession to produce selected fourth or higher backcross progeny plants that comprise the desired trait and all the physiological and morphological characteristics of alfalfa variety CW 104014.

The present disclosure is also directed to a method for producing an alfalfa plant having an altered agronomic trait relative to alfalfa variety CW 104014, as well as the plants and plant parts produced by such method. The method comprises introducing a polynucleotide into a CW 104014 plant grown from CW 104014 seed, representative seed of which has been deposited under ATCC Accession No: PTA-124567, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

DETAILED DESCRIPTION

Definitions

Terms used in the descriptions and tables that follow are defined as follows:

Acid Detergent Fiber ("ADF"). Acid detergent fiber approximates the amount of cellulose fiber and ash present in a feed. Forages with high ADF values are less digestible than forages with low ADF values and, therefore, provide fewer nutrients to the animal through digestion. Because of this relationship, ADF serves as an estimate of digestibility and can be used by nutritionists to predict the energy that will be available from a forage.

Acid Detergent Lignin ("ADL"). Acid detergent lignin is the lignin present in the residue following extraction with acid detergent. ADL is an estimate of lignin content. Lignin is an indigestible component of forage fiber (NDF) that is believed to limit the extent to which forage fiber can be digested by ruminant animals.

Crude Protein ("CP"). Crude Protein ("CP") is determined in part by measuring the total nitrogen concentration of a forage. This technique measures not only the nitrogen present in true proteins, but also that present in non-protein forms such as ammonia, urea and nitrate. Because most of the non-protein forms of nitrogen are converted to true protein by the rumen microorganisms, CP is considered by nutritionists to provide an accurate measure of the protein that will be available to ruminant animals from a given forage.

DM is the abbreviation for Dietary Dry Matter and used to calculate yield.

Digestible Neutral Detergent Fiber ("dNDF"). Digestible Neutral Detergent Fiber is the digestible fraction expressed as % of DM.

Enhance feed value and Relative Feed Value ("RFV") Enhance feed value refers to the forage quality, such as fiber content, digestibility, and available carbohydrate resources available to livestock. Enhanced feed value or alfalfa quality is determined by the Relative Feed Value (RFV) expressed as a percentage of alfalfa at 100% bloom and is used as a predictor of feed value in the field. Components that effect feed value are acid detergent lignin concentration and G lignin and neutral detergent fiber digestibility. The measurement of these feed value components is an aspect of the present disclosure.

Dyn Kd refers to the rate of fiber digestion or the digestibility rate.

Fall dormancy (FD). Most alfalfa plants go dormant in the fall in preparation for winter. The onset of dormancy is triggered by a combination of day length and temperature and is genotype dependent. Fall dormancy scores measure the dormancy response of alfalfa genotypes by quantifying how early dormancy is triggered. The standard fall dormancy test requires that plants are cut off in early September with plant height measured in mid-October. Early fall dormant types show very little growth after the September clipping, later fall dormant type demonstrate substantial growth. Alfalfa is classified into fall dormancy groups or classes numbered 1 through 11, where fall dormancy group 1 is very early fall dormant suited for cold climates and fall dormancy group 11 is very non-dormant and suited for very hot climates in which the plant would grow throughout the winter months. FD 1 is considered Very Dormant, FD 2 and FD3 are considered Dormant, FD 4, FD 5 and FD 6 are considered Moderately Dormant, FD7 and FD 8 are considered Non-Dormant, and FD 9, FD 10 and FD 11 are considered Very-Non-Dormant.

Forage yield is measured by harvesting herbage for part of or the entire life of the stand.

As used herein, "introduced into a plant" with respect to polynucleotides/traits includes introgressing the polynucleotides/traits into a plant by traditional breeding as well as the delivery of the polynucleotides/traits into a plant by transformation using recombinant DNA techniques.

In Vitro True Digestibility ("IVTD"). In Vitro True Digestibility is a measurement of digestibility utilizing actual rumen microorganisms.

In Vitro True Dry Matter Digestibility ("IVTDMD"). In Vitro True Dry Matter Digestibility measures the digestibility of the entire forage plant by incubating samples of the plant in rumen fluid taken from a cow, then boiling the incubated samples in neutral detergent to ensure that all non-fiber portions of the sample are removed. This procedure estimates how much of the total dry matter in a forage plant is actually digestible by the cow.

Milk Per Acre ("MA") and Milk Per Ton ("MT"). Milk Per Ton is an estimate of forage quality and milk production that could be supported by a given forage when fed as part of a total mixed ration. Milk per ton (lb/ton) is primarily driven by starch content, starch digestibility, and NDF digestibility. The equation for calculating milk per ton uses Neutral-Detergent Fiber ("NDF") and Acid-Detergent Fiber ("ADF") to calculate total energy intake possible from the forage. After subtracting the amount of energy required for daily maintenance of the cow, the quantity of milk that could be produced from the remaining energy is calculated. The ratio of milk produced to forage consumed is then reported in the units of pounds of milk produced per ton of forage consumed. Milk per ton is useful because it characterizes forage quality in two terms that a dairy farmer is familiar with: pounds of milk and tons of forage. "Milk Per Acre" is determined by combining milk per ton and dry matter yield per acre (lb/acre). Milk per acre is calculated by multiplying milk per ton times dry matter yield per acre. These terms are widely used to estimate the economic value of a forage.

Neutral-Detergent Fiber ("NDF"). Neutral-Detergent Fiber represents the total amount of fiber present in the alfalfa. "aNDF" refers to amylase-treated neutral detergent fiber.

"Neutral Detergent Fiber Digestibility" (NDFD). Neutral Detergent Fiber Digestibility (NDFD) refers to the content of forage is a measure of the digestibility of a forage fiber as % of NDF, and can be measured in vitro and predicted using Near Infrared Reflectance Spectroscopy (NIRS). NDFD is the digestible fraction expressed as % of NDF. The higher the NDFD value the more digestible the forage. NDFD represents the indigestible and slowly digestible components in plant cell wall (cellulose, hemicellulose, lignin (units=% of dry matter)). dNDF may be used to calculate NDFD.

Persistence is a measurement of the ability of the variety to last over a minimum of two years. This measurement is documented in the visual percent stand remaining at the time of observation.

As used herein, the term "plant" includes plant cells, plant protoplasts, plant cells of tissue culture from which alfalfa plants can be regenerated, plant calli, plant clumps, and plant cells that are intact in plants or parts of plants such as pollen, flowers, seeds, leaves, stems, and the like.

Relative Forage Quality ("RFQ"). Relative Forage Quality ("RFQ") is a numeric value that estimates the energy content of forage for total digestible nutrients as recommended by the National Research Council. Values are assigned to forages based upon the actual fiber digestibility (NDFD) and Total Digestible Nutrients (TDN). By combining these two relationships, an estimate of how the forage will perform in animal rations is predicted. Relative forage quality has been accepted in many areas as a means of estimating forage feeding value and is commonly used in determining the price of alfalfa at tested hay auctions or for on farm use.

Synthetic variety ("SYN"). SYN variety is developed by intercrossing a number of genotypes with specific favorable characteristics and/or overall general favorable qualities. SYN variety can be developed by using clones, inbreds, open pollinated varieties, and/or individual heterozygous plants.

TA is the abbreviation for Tons per Acre and is used to calculate yield.

Total Digestible Nutrients. Total Digestible Nutrients ("TDN") is an estimate of the energy content of a feedstuff based on its relative proportions of fiber, fat, carbohydrate, crude protein, and ash. Because it is expensive to measure each of these components, TDN is usually estimated from ADF or IVTD. TDN may overestimate the energy content of low quality forages and thus may not accurately reflect the nutritional value of all forage samples.

Total Tract NDF Digestibility ("TTNDFD"). Total Tract NDF Digestibility ("TTNDFD") is a tool that combines feed (feed fiber—potentially digestible NDF rate of fiber digestion) and cow (fiber digestion—rate of passage) factors to measure energy from fiber. It is a calculation that uses several time points of NDFD, for example, after 24, 30, or 48 hours, combined with the rate of fiber digestion, the rate of fiber passage and also indigestible fiber, therefore giving a better picture of fiber digestibility as a whole. The calculation is calibrated to a cow producing 85 pounds of milk. A 2-3 unit change in ration TTNDFD corresponds to a one-pound change in milk yield.

Weighted mean. Weighted mean is similar to an arithmetic mean where instead of each of the data points contributing equally to the final average, some data points contribute more than others.

Winterhardiness ("WH") is a measure of the ability of an alfalfa plant to survive the stresses associated with winter. Cold hardiness is a key feature of the winterhardiness trait. There is a general relationship between fall dormancy and winterhardiness, the early fall dormant types (FD2-5) being more winterhardy than the later fall dormant types (FD6-9). The winterhardiness rating used in this disclosure are derived from the standard test for measuring winter survival. The standard test measures plant survival and spring vigor following a winter stress enough to substantially injure known commercial varieties.

EMBODIMENTS

In accordance with one embodiment an alfalfa variety is provided having at least about 5.0% to at least about 25.0% less total lignin content compared to a control alfalfa variety (e.g., PIONEER 55V12) grown under the same field growing conditions. In accordance with one embodiment a low Acid Detergent Lignin (ADL) alfalfa variety is provided comprising about 5.0% to about 25% less acid detergent lignin content relative to a control alfalfa variety (e.g., PIONEER 55V12) grown under the same field growing conditions. The lignin content may be measured about 21 days after clipping, about 22 days after clipping, about 28 days after clipping, about 29 days after clipping, about 35 days after clipping, or about 42 days after clipping. The lignin content may be measured in the lower stems or in the whole plant of the alfalfa plant. The alfalfa variety may have at least about 5.0% to about 25.0% more total digestible nutrient, 5.0% to about 25.0% more relative forage quality, 5.0% to about 25.0% more relative forage value, or 5.0% to about 25.0% more milk per ton of dry mass compared to the commercial alfalfa variety (e.g., PIONEER 55V12) grown under the same field growing conditions. The total digestible nutrient may be measured as in vitro total dry matter digestibility, neutral detergent fiber digestibility, or total tract neutral detergent fiber digestibility. The total digestibility nutrient may be measured about 21 days after clipping, about 22 days after clipping, about 28 days after clipping, about 29 days after clipping, about 35 days after clipping, or about 42 days after clipping. The control alfalfa variety may be a commercial alfalfa variety. The commercial alfalfa variety may be selected from the group consisting of 55V12, Althea, Cornerstone, HybriForce-2400, HybriForce-3400, Keystone II, Magnum 7, Magnum 7-Wet, N-R-Gee, PGI 212, VR TOTAL, PGI 529 (DOMINATOR), PGI 557 (LELIA), PILLAR ST, ROBUST, StarGold, and WL 319 HQ.

In one embodiment the present disclosure is directed to seed of alfalfa variety CW 104014, representative seed having been deposited under ATCC Accession Number PTA-124567. The present disclosure is also directed to a plant, or a part thereof (including pollen, ovule or seed), produced by growing seed of alfalfa variety CW 104014 as well as F1 progeny of a plant grown from the seed of alfalfa variety CW 104014, wherein the F1 progeny having retained the low ADL levels of alfalfa variety CW 104014 and/or all the physiological and morphological characteristics of alfalfa variety CW 104014.

Alfalfa variety CW 104014 is a synthetic variety developed by Alforex Seeds with 12 parent plants selected for low Acid Detergent Lignin (ADL), high forage dry matter yield, high forage milk per acre using Milk 2000, and/or high forage NDFD. Parent plants were selected from a three-year-old Wisconsin selection nursery, crossed in the greenhouse, and bulk harvested as Synthetic generation 1. Nursery source plants composed of various populations that were developed by phenotypic recurrent selection for low Acid Detergent Lignin (ADL), winter hardiness, high forage dry matter yield, high NDFD (using Near Infrared Reflectance Spectroscopy), and for resistance to one or more of the following pests: bacterial wilt, *Fusarium* Wilt, *Verticillium* wilt, *Phytophthora* root rot, *Aphanomyces* root rot (race 1), *Aphanomyces* root rot (race 2), Anthracnose (race 1), and *Leptosphaerulina* leaf spot.

Alfalfa variety CW 104014 has been tested for forage yield and winterhardiness in Iowa, Minnesota, and Wisconsin, and is intended for use in the North Central, East Central, Great Plains, Moderately Winterhardy Intermountain and Winterhardy Intermountain areas of the U.S.

Alfalfa variety CW 104014 is Moderately Dormant, similar to FD4 check. Flower color (Syn 2) is 99% purple, with a trace of cream, variegated, yellow and white. CW 104014 has Low multifoliolate leaf expression rating similar to the Low MF check variety. CW 104014 has high resistance to Anthracnose (race 1), *Aphanomyces* root rot (race 1), Bacterial wilt, *Fusarium* wilt, *Phytophthora* root rot, *Verticillium* wilt, and Stem Nematode. It has resistance to *Aphanomyces* root rot (race 2). Reaction to Blue alfalfa aphid, Spotted alfalfa aphid, Pea aphid, and root knot nematode has not been tested. This variety is suitable for use in producing hay, haylage, greenchop, and dehydrated product.

Use of CW 104014 in Alfalfa Breeding

Another aspect of the present disclosure provides a method for producing first-generation synthetic variety alfalfa seed comprising crossing a first parent alfalfa plant with a second parent alfalfa plant and harvesting resultant first-generation (F1) alfalfa seed, wherein said first or second parent alfalfa plant is alfalfa variety CW 104014.

Male Sterility

The present disclosure also provides a method of obtaining alfalfa populations using cytoplasmic male sterile alfalfa populations (A populations), maintainer alfalfa populations (B populations), and male fertile pollenizer populations (C populations). Male sterile A populations may be identified by evaluating pollen production using the Pollen Production Index (P.P.I.), which recognizes four distinct classes: 1. Male Sterile Plants (MS) PPI=0 No visible pollen can be observed with the naked eye when flower is tripped with a black knife blade. 2. Partial Male Sterile Plant (PMS) PPI=0.1 A trace of pollen is found with the naked eye when flower is tripped with a black knife blade. 3. Partial Fertile Plant (PF) PPI=0.6 Less than a normal amount of pollen can be observed with the naked eye when flower is tripped with a black knife blade. 4. Fertile Plant (F) PPI=1.0 Normal amounts of pollen can be observed when flower is tripped with a black knife blade.

The cells of the cytoplasmic male sterile (A population) alfalfa plants contain sterile cytoplasm and the non-restorer gene. The maintainer population (B population) is a male and female fertile plant, and when crossed with an A population plant, maintains the male sterility of the cytoplasmic male sterile plant in the progeny. The cells of a maintainer population plant contain normal cytoplasm and the non-restorer gene. Methods for identifying cytoplasmic male sterile and maintainer populations of alfalfa are well known to those versed in the art of alfalfa plant breeding (e.g., see U.S. Pat. No. 3,570,181, which is incorporated by reference herein). A pollenizer population (C population) is a fertile plant containing both male and female parts.

Cytoplasmic male sterile populations may be maintained by vegetative cuttings. Maintainer populations can be maintained by cuttings or self-pollination. Male sterile plants can be obtained by cross-pollinating cytoplasmic male sterile plants with maintainer plants. Pollenizer populations can be maintained by selfing or, if more than two clones are used, by cross-pollination.

Preferably, at least one of the alfalfa plant populations used in developing alfalfa plants according to the method of the present disclosure has at least one desirable agronomic trait, which may include, for example, resistance to disease or insects, cold tolerance, increased persistence, greater forage yield or seed yield, improved forage quality, uniformity of growth rate, and uniformity of time of maturity.

In the controlled pollination step, the cytoplasmic male sterile plants are typically grown in separate rows from the maintainer plants. The plants are pollinated by pollen-carrying insects, such as bees. Segregating the male sterile and maintainer plants facilitates selective harvest of seed from the cytoplasmic male sterile plants.

The male sterile seed and male fertile seed is preferably provided as a random mixture of the seed in a ratio of about 4:1, which would provide for random distribution of the male sterile and male fertile plants grown therefrom and random pollination of the alfalfa plants. As one of skill in the art will appreciate, one could also practice the method of the present disclosure using designed distribution of male sterile and male fertile populations within a field and subsequent pollination by pollen-carrying insects.

One of ordinary skill in the art will appreciate that any suitable male sterile population, maintainer population, and pollenizer population could be successfully employed in the practice of the method of the present disclosure.

Tissue Culture

Yet another embodiment a tissue culture of regenerable cells derived, in whole or in part, from an alfalfa plant of synthetic variety named CW 104014 is provided. In one such embodiment, the cells regenerate plants having substantially all the morphological and physiological characteristics of the synthetic alfalfa variety named CW 104014 that are described in the attached tables. Some embodiments include such a tissue culture that includes cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. Another embodiment is an alfalfa plant regenerated from such a tissue culture, having all the morphological and physiological characteristics of synthetic alfalfa variety CW 104014.

Some methods for the regeneration of alfalfa plants from tissue culture are described in U.S. Pat. No. 5,324,646 issued Jun. 28, 1994, which is hereby incorporated by reference. Additionally, researchers believe that somatic embryogenesis in alfalfa is heritable, and is controlled by relatively few genes. Efforts at improving regeneration have thus been directed towards isolation of the genetic control of embryogenesis, and breeding programs which would incorporate such information. See, e.g., M. M. Hernandez-Fernandez, and B. R. Christie, Genome 32:318-321 (1989); I. M. Ray and E. T. Bingham, Crop Science 29:1545-1548 (1989). Tissue culture of alfalfa is further described in Saunders, J. W. and Bingham, E. T., (1971) Production of alfalfa plants from callus tissue is described in Crop Sci 12; 804-808, and is incorporated herein by reference.

Transformation

Any DNA sequences, whether from a different species or from the same species, which are inserted into the genome using transformation are referred to herein collectively as "transgenes". In some embodiments of the present disclosure, a transformed variant of CW 104014 may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present disclosure also relates to transformed versions of the claimed alfalfa variety CW 104014 as well as hybrid progeny thereof.

Numerous methods for plant transformation have been developed, including biological and physical plant transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). Specific to alfalfa, see "Efficient *Agrobacterium*-mediated transformation of alfalfa using secondary somatic embryogenic callus", Journal of the Korean Society of Grassland Science 20 (1): 13-18 2000, E. Charles Brummer, "Applying Genomics to Alfalfa Breeding Programs" Crop Sci. 44:1904-1907 (2004), and "Genetic transformation of commercial breeding populations of alfalfa (*Medicago sativa*)" Plant Cell Tissue and Organ Culture 42 (2): 129-140 1995 which are incorporated by reference for this purpose. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements. Promoters that may be used include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described herein. Suitable promoters include, without limitation, the 35S promoter of the cauliflower mosaic virus, ubiquitin, tCUP cryptic constitutive promoter, the Rsyn7 promoter, pathogen-inducible promoters, the maize In2-2 promoter, the tobacco PR-la promoter, glucocorticoid-inducible promoters, and tetracycline-inducible and tetracycline-repressible promoters.

A genetic trait which has been engineered into the genome of a particular alfalfa plant using transformation techniques, could be moved into the genome of another population using traditional breeding techniques that are well known in the plant breeding arts. For example, a backcrossing approach may be used to move a transgene from a transformed alfalfa plant to an elite population, and the resulting progeny would then comprise the transgene(s).

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. No. 6,118,055.

With transgenic plants according to the present disclosure, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114: 92-6 (1981).

Through the transformation of alfalfa, the expression of genes can be altered to enhance disease resistance, insect resistance, herbicide resistance, agronomic, grain quality and other traits. Transformation can also be used to insert DNA sequences which control or help control male-sterility. DNA sequences native to alfalfa as well as non-native DNA sequences can be transformed into alfalfa and used to alter levels of native or non-native proteins. Various promoters, targeting sequences, enhancing sequences, and other DNA sequences can be inserted into the alfalfa genome for the purpose of altering the expression of proteins. Reduction of the activity of specific genes (also known as gene silencing, or gene suppression) is desirable for several aspects of genetic engineering in plants. Methods suitable for introducing polynucleotides into a plant useful in the practice of the present invention are well known in the art and include, but are not limited to, freeze-thaw method, microparticle bombardment, direct DNA uptake, whisker-mediated transformation, electroporation, sonication, microinjection, plant virus-mediated, and *Agrobacterium*-mediated transfer to the plant. Any suitable *Agrobacterium* strain, vector, or vector system for transforming the plant may be employed according to the present invention.

Exemplary nucleotide sequences that may be altered by genetic engineering include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium flavum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*); McDowell & Woffenden, (2003) Trends Biotechnol. 21(4): 178-83 and Toyoda et al., (2002) Transgenic Res. 11(6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and Ser. No. 10/606,320.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, J. Biol. Chem. 269: 9 (1994) (expression cloning yields DNA coding for insect diuretic hormone receptor); Pratt et al., Biochem. Biophys. Res. Comm 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini & Grossi-de-Sa (2002) Toxicon, 40 (11): 1515-1539; Ussuf et al. (2001) Curr Sci. 80 (7): 847-853; and Vasconcelos & Oliveira (2004) Toxicon 44 (4): 385-403. See also U.S. Pat. No. 5,266,317 to Tomalski et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23: 691 (1993), who teach the nucleotide sequence of a cDNA encoding tobacco hookworm chitinase, and Kawalleck et al., Plant Molec. Biol. 21: 673 (1993), who provide the nucleotide sequence of the parsley ubi4-2 polyubiquitin gene, U.S. application Ser. Nos. 10/389,432, 10/692,367, and U.S. Pat. No. 6,563,020.

(G) A molecule that stimulates signal transduction. For example, see the disclosure by Botella et al., Plant Molec. Biol. 24: 757 (1994), of nucleotide sequences for mung bean calmodulin cDNA clones, and Griess et al., Plant Physiol. 104: 1467 (1994), who provide the nucleotide sequence of a maize calmodulin cDNA clone.

(H) A hydrophobic moment peptide. See PCT application WO 95/16776 and U.S. Pat. No. 5,580,852 (disclosure of peptide derivatives of Tachyplesin which inhibit fungal plant pathogens) and PCT application WO 95/18855 and U.S. Pat. No. 5,607,914) (teaches synthetic antimicrobial peptides that confer disease resistance).

(I) A membrane permease, a channel former or a channel blocker. For example, see the disclosure by Jaynes et al., Plant Sci. 89: 43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol. 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., Nature 366: 469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., Bio/Technology 10: 1436 (1992). The cloning and characterization of a gene which encodes a bean endopolygalacturonase-inhibiting protein is described by Toubart et al., Plant J. 2: 367 (1992).

(N) A developmental-arrestive protein produced in nature by a plant. For example, Logemann et al., Bio/Technology 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2):128-131 (1995), Pieterse & Van Loon (2004) Curr. Opin. Plant Bio. 7(4):456-64 and Somssich (2003) Cell 113(7):815-6.

(P) Antifungal genes (Cornelissen and Melchers, PI. Physiol. 101:709-712, (1993) and Parijs et al., Planta 183: 258-264, (1991) and Bushnell et al., Can. J. of Plant Path. 20(2):137-149 (1998). Also see U.S. application Ser. No. 09/950,933.

(Q) Detoxification genes, such as for fumonisin, beauvericin, moniliformin and zearalenone and their structurally related derivatives. For example, see U.S. Pat. No. 5,792,931.

(R) Cystatin and cysteine proteinase inhibitors. See U.S. application Ser. No. 10/947,979.

(S) Defensin genes. See WO03000863 and U.S. application Ser. No. 10/178,213.

(T) Genes conferring resistance to nematodes. See WO 03/033651 and Urwin et al., Planta 204:472-479 (1998), Williamson (1999) Curr Opin Plant Bio. 2(4):327-31.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee et al., EMBO J. 7: 1241 (1988), and Mild et al., Theor. Appl. Genet. 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,566,587; 6,338, 961; 6,248,876 B1; 6,040,497; 5,804,425; 5,633,435; 5,145, 783; 4,971,908; 5,312,910; 5,188,642; 4,940,835; 5,866, 775; 6,225,114 B1; 6,130,366; 5,310,667; 4,535,060; 4,769, 061; 5,633,448; 5,510,471; Re. 36,449; RE 37,287 E; and 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. application Ser. Nos. 01/462,27; 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., Bio/Technology 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cycloshexones, such as sethoxydim and haloxyfop, are the Acc1-S1, Acc1-S2 and Acc1-S3 genes described by Marshall et al., Theor. Appl. Genet. 83: 435 (1992).

(C) A herbicide that inhibits photosynthesis, such as a triazine (psbA and gs+ genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet 246:419). Other genes that confer resistance to herbicides include: a gene encoding a chimeric protein of rat cytochrome P4507A1 and yeast NADPH-cytochrome P450 oxidoreductase (Shiota et al. (1994) Plant Physiol. 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Transgenes that Confer or Contribute to an Altered Grain Characteristic, Such as:

(A) Altered fatty acids, for example, by (1) Down-regulation of stearoyl-ACP desaturase to increase stearic acid content of the plant. See Knultzon et al., Proc. Natl. Acad. Sci. USA 89: 2624 (1992) and WO99/64579 (Genes for Desaturases to Alter Lipid Profiles in Corn), (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245), (3) Altering conjugated linolenic or linoleic acid content, such as in WO 01/12800, (4) Altering LEC1, AGP, Dek1, Superal1, mi1ps, various Ipa genes such as Ipa1, Ipa3, hpt or hggt. For example, see WO 02/42424, WO 98/22604, WO 03/011015, U.S. Pat. Nos. 6,423,886, 6,197,561, 6,825, 397, US2003/0079247, US2003/0204870, WO02/057439, WO03/011015 and Rivera-Madrid, R. et. al. Proc. Natl. Acad. Sci. 92:5620-5624 (1995).

(B) Altered phosphorus content, for example, by the (1) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene. (2) Up-regulation of a gene that reduces phytate content. In alfalfa, this, for example, could be accomplished, by cloning and then re-introducing DNA associated with one or more of the alleles, such as the LPA alleles, identified in maize mutants characterized by low levels of phytic acid, such as in Raboy et al., Maydica 35: 383 (1990) and/or by altering inositol kinase activity as in WO 02/059324, US2003/0009011, WO 03/027243, US2003/0079247, WO 99/05298, U.S. Pat. Nos. 6,197,561, 6,291,224, 6,391,348, WO2002/059324, US2003/0079247, Wo98/45448, WO99/55882, WO01/04147.

(C) Altered carbohydrates effected, for example, by altering a gene for an enzyme that affects the branching pattern of starch or a gene altering thioredoxin (See U.S. Pat. No. 6,531,648). See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus licheniformis* alpha-amylase), Elliot et al., Plant Molec.

Biol. 21: 515 (1993) (nucleotide sequences of tomato invertase genes), Sogaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640; all of which are hereby incorporated by reference.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of E. coli (Enomoto et al., 1983), and the R/RS system of the pSR1 plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. Nos. 6,177,275, and 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. No. 6,794,560, 6,307,126 (GAI), WO99/09174 (D8 and Rht), and WO2004076638 and WO2004031349 (transcription factors).

Forage Yield Data for Alfalfa Variant CW 104014 is Provided in Table 1A & B

TABLE 1A

Total Yield (DM in T/A)

| Test Location | Date Planted Mo/Yr | Syn Gen | Year Harvested | No. Cuts | CW 104014 | 55V12 | Hybri-Force 400 | WL 319 HQ | LSD .05 | CV % |
|---|---|---|---|---|---|---|---|---|---|---|
| West Salem, WI | December 2011 | 2 | 2012 | 5 | 9.20 | 8.34 | 8.24 | 8.34 | 0.55 | 3.86 |
| | | | 2013 | 5 | 8.56 | 7.40 | 7.28 | 7.28 | 0.78 | 6.12 |
| | | | 2014 | 4 | 8.74 | 7.28 | 6.26 | 6.73 | 0.73 | 5.73 |
| Decorah, IA | December 2011 | 2 | 2012 | 5 | 8.73 | 8.94 | 9.02 | 9.15 | 0.87 | 5.85 |
| | | | 2013 | 4 | 7.29 | 6.64 | 6.53 | 6.80 | 1.00 | 8.88 |
| Medford, MN | December 2011 | 2 | 2012 | 5 | 6.85 | 6.17 | 6.10 | 6.77 | 0.61 | 5.67 |
| | | | 2013 | 3 | 3.21 | 3.47 | 3.39 | 3.24 | 0.53 | 9.73 |
| Madison, WI | December 2011 | 2 | 2012 | 5 | 9.51 | 9.04 | 9.46 | 9.78 | 0.91 | 5.71 |
| | | | 2013 | 4 | 7.70 | 7.53 | 6.60 | 6.32 | 1.49 | 13.50 |

TABLE 1B

Mean Annual Yield

| | | | Tons DM/Acre | | | |
|---|---|---|---|---|---|---|
| Variety names | # of Years Harvested | Total # of Harvests | CW 104014 | 55V12 | Hybri-Force 400 | WL 319 HQ |
| CW 104014 | 9 | 40 | 7.75 | | | |
| Check 1 (55V12) | 9 | 40 | 7.75 | 7.20 | | |
| Check 2 (Hybri-Force 400) | 9 | 40 | 7.75 | | 6.99 | |
| Check 3 (WL 319 HQ) | 9 | 40 | 7.75 | | | 7.16 |

TABLE 1C

Forage Quality Summary. CW 104014 compared to check varieties.

Forage Quality Summary. CW 104014 compared to check varieties.

| | | | | | CW 104014 % of Check Mean | | | |
|---|---|---|---|---|---|---|---|---|
| Worksheet | Trial ID | Location | Cut Mngmt | Hay Year | CP | ADL | uNDF 240 | kD |
| Test 7374'!A1 | 7374 | Wslm, WI | Regular | Year 1 | −1.9% | −5.8% | | |
| Test 7983 28 DAC'!A1 | 7983 | Wslm, WI | Early | Year 1 | 1.1% | −3.7% | | |
| Test 7984 35 DAC'!A1 | 7984 | Wslm, WI | Medium | Year 1 | 4.8% | −15.4% | | |
| Test 7985 42 DAC'!A1 | 7985 | Wslm, WI | Late | Year 1 | 7.3% | −10.2% | | |
| Test 8112 E'!A1 | 8112 | Wslm, WI | Early | Year 1 | 8.2% | −5.5% | | |
| Test 8115 L'!A1 | 8115 | Wslm, WI | Medium | Year 1 | 10.2% | −7.1% | | |
| Test 8118 L'!A1 | 8118 | Wslm, WI | Late | Year 1 | 8.5% | −4.2% | | |
| Test 8235 E'!A1 | 8235 | Wslm, WI | Early | Year 1 | 0.7% | −6.3% | −7.4% | 8.6% |
| Test 8239 L'!A1 | 8239 | Wslm, WI | Late | Year 1 | 3.1% | −11.6% | 12.7% | 5.6% |
| | | Average | | | 4.7% | −7.8% | 10.0% | 7.1% |

| | | CW 104014 % of Check Mean | | | | | |
|---|---|---|---|---|---|---|---|
| Worksheet | Trial ID | TTNDFD | NDFD48 | TDN | RFV | RFQ | M/Ton | M/Acre |
| Test 7374'!A1 | 7374 | | 2.5% | 1.5% | 3.5% | 4.9% | 2.4% | 4.3% |
| Test 7983 28 DAC'!A1 | 7983 | | 2.1% | 1.2% | 3.7% | 4.6% | 1.9% | |
| Test 7984 35 DAC'!A1 | 7984 | | 6.4% | 4.3% | 14.4% | 17.4% | 6.7% | |
| Test 7985 42 DAC'!A1 | 7985 | | 3.8% | 2.1% | 9.8% | 10.7% | 3.0% | |
| Test 8112 E'!A1 | 8112 | | 4.5% | 0.8% | 6.6% | 7.3% | 0.7% | −2.4% |
| Test 8115 L'!A1 | 8115 | | 7.8% | 3.6% | 9.2% | 13.6% | 5.0% | 4.3% |

TABLE 1C-continued

Forage Quality Summary. CW 104014 compared to check varieties.

Forage Quality Summary. CW 104014 compared to check varieties.

| Test 8118 L'!A1 | 8118 |  | 4.4% | 0.9% | 4.8% | 6.4% | 0.5% | −6.7% |
|---|---|---|---|---|---|---|---|---|
| Test 8235 E'!A1 | 8235 | 7.2% | 5.1% | 1.8% | 4.4% | 7.3% | 2.5% | 4.5% |
| Test 8239 L'!A1 | 8239 | 9.5% | 7.2% | 4.1% | 10.6% | 15.1% | 6.2% | 6.9% |
|  | Average | 8.4% | 4.9% | 2.3% | 7.4% | 9.7% | 3.2% | 1.8% |

TABLE 2

% Stand

| Test Location | Syn Gen | Date Seeded Mo/Yr | No. of Years Harvested | No. of Harvests | Date of Readings (Mo/Yr) Initial/Final | CW 104014 Initial/Final | 55V12 Initial/Final | WL 319 HQ Initial/Final | LSD .05 | CV % |
|---|---|---|---|---|---|---|---|---|---|---|
| Medford, MN | 2 | May 2011 | 3 | 11 | September 2011 / September 2013 | 99/73 | 99/73 | 99/70 | 8.18 | 7.0 |
| West Salem, WI | 2 | May 2011 | 4 | 18 | September 2011 / September 2014 | 99/87 | 99/50 | 99/68 | 12.45 | 10.7 |

Multifoliolate Leaf Expression of Alfalfa Variant CW 104014 is Presented in Table 3

Test Conducted by Alforex Seeds at West Salem, Wis.

TABLE 3

| Variety | MFI | Range | Multifoliolate Leaf Expression Score | Year Tested | Syn Gen | MFI | % MF |
|---|---|---|---|---|---|---|---|
| CW 104014 |  |  | 1.84 | 2011 | 2 | 1.92 | 51 |
| 1. Vernal | 1.00 | 1.00-1.05 | 1.03 |  |  | 1.07 | 09 |
| 2. Legend | 1.86 | 1.40-2.40 | 1.42 |  |  | 1.48 | 29 |
| 3. MultiKing I | 2.55 | 2.00-3.00 | 2.18 |  |  | 2.26 | 78 |
| 4. Proof | 3.35 | 2.80-3.80 | 3.22 |  |  | 3.35 | 89 |
| Test Mean: 1.61 |  |  |  |  |  | 1.68 | 39 |
| L.S.D. (.05%) 0.39 |  |  |  |  |  | 0.40 | 22 |
| C.V. (%) |  |  | 14.77 |  |  | 14.77 | 35 |

CW 104014 is most similar in multifoliolate leaf expression to the Legend check variety showing low MF

TABLE 4

Fall dormancy as determined from spaced plantings relative to three (3) standard check varieties.

| Test Location Wes Salem, WI | FDC[1] | Score or Average Height — Dormancy Score or Average Height | Syn Gen | Date of Last Cut (Mo/Yr) | Date Measured (Mo/Yr) | LSD .05 | CV % |
|---|---|---|---|---|---|---|---|
| Fall Dormancy Class for CW 104014 |  | 23.50 | 2 | September 2011 | October 2011 | 2.01 | 5.22 |
| Check Varieties — enter data next to appropriate check variety |  |  |  |  |  |  |  |
| Maverick | 1.0 |  |  |  |  |  |  |
| Vernal | 2.0 |  |  |  |  |  |  |
| 5246 | 3.0 | 21.92 |  |  |  |  |  |
| Legend | 4.0 | 24.17 |  |  |  |  |  |
| Archer | 5.0 | 27.33 |  |  |  |  |  |

TABLE 4-continued

Fall dormancy as determined from spaced plantings relative to three (3) standard check varieties.

| Test Location Wes Salem, WI | FDC[1] | Dormancy Score or Average Height | Syn Gen | Date of Last Cut (Mo/Yr) | Date Measured (Mo/Yr) | LSD .05 | CV % |
|---|---|---|---|---|---|---|---|
| ABI 700 | 6.0 | | | | | | |
| Doña Ana | 7.0 | | | | | | |
| Pierce | 8.0 | | | | | | |
| CUF 101 | 9.0 | | | | | | |
| UC-1887 | 10.0 | | | | | | |
| UC-1465 | 11.0 | | | | | | |

Pest Reaction Characteristics

| | Variety | Resistance Class | Year Tested | Syn Gen | Unadjusted % R | Adjusted % R | Score |
|---|---|---|---|---|---|---|---|
| | ANTHRACNOSE DISEASE (Race 1) Greenhouse testing Test conducted by Alforex Seeds at West Salem, WI | | | | | | |
| | CW 104014 | HR | 2015 | 2 | 56 | 58 | |
| 1. | Arc | HR | | | 63 | 65 | |
| 2. | Saranac AR | R | | | 49 | 51 | |
| 3. | Saranac | S | | | 3 | 3 | |
| | Test Mean: | | | | 54 | 56 | |
| | L.S.D. (.05%) | | | | 14 | 14 | |
| | C.V. (%) | | | | 18 | 18 | |
| | BACTERIAL WILT DISEASE Field testing Test conducted by Alforex Seeds at West Salem, WI | | | | | | |
| | CW 104014 | HR | 2015 | 2 | 63 | 78 | 2.32 |
| 1. | Vernal | R | | | 34 | 42 | 3.42 |
| 2. | Narragansett | S | | | 1 | 1 | 4.34 |
| 3. | Sonora | S | | | 3 | 4 | 4.04 |
| | Test Mean: | | | | 44 | 54 | 2.86 |
| | L.S.D. (.05%) | | | | 11 | 13 | 0.31 |
| | C.V. (%) | | | | 17 | 17 | 7.66 |
| | FUSARIUM WILT DISEASE Field testing Test conducted by Alforex Seeds at West Salem, WI | | | | | | |
| | CW 104014 | HR | 2015 | 2 | 61 | 70 | 2.55 |
| 1. | Agate Field | HR | | | 47 | 54 | 3.18 |
| 2. | Moapa 69 Field | HR | | | 68 | 78 | 2.37 |
| 3. | Narragansett Field | MR | | | | | |
| 4. | MNGN-1 | S | | | 3 | 4 | 4.81 |
| | Test Mean: | | | | 54 | 61 | 2.79 |
| | L.S.D. (.05%) | | | | 12 | 14 | 0.39 |
| | C.V. (%) | | | | 16 | 16 | 9.88 |
| | VERTICILLIUM WILT DISEASE Greenhouse testing Test conducted by Alforex Seeds at West Salem, WI | | | | | | |
| | CW 104014 | HR | 2015 | 2 | 53 | 55 | 2.48 |
| 1. | Vertus | R | | | 42 | 43 | 2.77 |
| 2. | Oneida VR | HR | | | 58 | 60 | 2.44 |
| 3. | Saranac | S | | | 3 | 3 | 3.77 |
| | Test Mean: | | | | 47 | 49 | 2.63 |
| | L.S.D. (.05%) | | | | 11 | 11 | 0.22 |
| | C.V. (%) | | | | 16 | 16 | 5.80 |
| | PHYTOPHTHORA ROOT ROT DISEASE Seedling testing Test conducted by Alforex Seeds at West Salem, WI | | | | | | |
| | CW 104014 | HR | 2015 | 2 | 66 | 65 | |
| 1. | WAPH-1 (seedling) | HR | | | 56 | 55 | |
| 2. | MNP-D1 (seedling) | R | | | | | |
| 3. | Agate | R | | | | | |
| 4. | Saranac | S | | | 2 | 2 | |

| | Pest Reaction Characteristics | | | | | |
|---|---|---|---|---|---|---|
| Variety | Resistance Class | Year Tested | Syn Gen | Unadjusted % R | Adjusted % R | Score |
| Test Mean: | | | | 42 | 41 | |
| L.S.D. (.05%) | | | | 9 | 9 | |
| C.V. (%) | | | | 19 | 19 | |
| APHANOMYCES ROOT ROT DISEASE | | | Race 1 __X__ Race 2 _____ | | | |
| Greenhouse testing | | | | | | |
| Test conducted by Alforex Seeds at West Salem, WI | | | | | | |
| CW 104014 | HR | 2015 | 2 | 55 | 61 | 2.36 |
| 1. WAPH-1 (Race 1) | R | | | 45 | 50 | 2.46 |
| 2. WAPH-1 (Race 2) | S | | | | | |
| 3. WAPH-5 (Race 2) | R | | | | | |
| 4. Saranac (Races 1 & 2) | S | | | 3 | 4 | 3.32 |
| Test Mean: | | | | 50 | 56 | 2.49 |
| L.S.D. (.05%) | | | | 11 | 13 | 0.37 |
| C.V. (%) | | | | 18 | 18 | 11.86 |
| APHANOMYCES ROOT ROT DISEASE | | | | | | |
| Greenhouse testing | | | | | | |
| Test conducted by Alforex Seeds at West Salem, WI | | | | | | |
| CW 104014 | R | 2016 | 2 | 44 | 38 | 2.55 |
| 1. WAPH-1 (Race 1) | R | | | | | |
| 2. WAPH-1 (Race 2) | S | | | 4 | 3 | 3.21 |
| 3. WAPH-5 (Race 2) | R | | | 58 | 50 | 2.16 |
| 4. Saranac (Races 1 & 2) | S | | | 3 | 2 | 3.39 |
| Test Mean: | | | | 39 | 34 | 2.65 |
| L.S.D. (.05%) | | | | 12 | 10 | 0.26 |
| C.V. (%) | | | | 21 | 21 | 6.91 |
| STEM NEMATODE | | | | | | |
| Kind of test conducted: Controlled environment GH | | | | | | |
| Test conducted by Alforex Seeds at Woodland, CA | | | | | | |
| CW 104014 | R | 2015 | 2 | 49 | 56 | |
| 1. Vernema | HR | | | 52 | 60 | |
| 2. Lahontan | R | | | | | |
| 3. Lew | R | | | | | |
| 4. Ranger | S | | | 10 | 12 | |
| 5. Moapa 69 | S | | | | | |
| Test Mean: | | | | 46 | 53 | |
| L.S.D. (.05%) | | | | 20 | 23 | |
| C.V. (%) | | | | 30 | 30 | |

DEPOSITS

Applicant has made a deposit under the Budapest Treaty of at least 2500 seeds of Alfalfa, *Medicago sativa*, Variant CW 104014 with the American Type Culture Collection (ATCC), 10801 University Boulevard, Manassas, Va. 20110-2209, USA. The deposit was made on Nov. 3, 2017 and the deposited seed were assigned ATCC Deposit No. PTA-124567. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. 1.808. This deposit of the Alfalfa Variety CW 104014 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

What is claimed is:

1. A seed of alfalfa variety CW 104014, or a part thereof, wherein representative seed of the variety have been deposited under ATCC Accession No. PTA-124567.

2. A population of alfalfa seeds, the population comprising the seed of claim 1.

3. A plant of alfalfa variety CW 104014, or a plant part thereof, wherein representative seed of the variety have been deposited under ATCC Accession No. PTA-124567.

4. A pollen grain or an ovule of the plant or plant part of claim 3.

5. A tissue culture of regenerable cells or regenerable protoplasts produced from the plant or plant part of claim 3.

6. A method for producing alfalfa seed, the method comprising: (a) growing the plant of claim 3 under pollinating conditions; and (b) harvesting seed produced by the plant grown in step (a).

7. An alfalfa seed, or a plant grown therefrom, produced by the method of claim 6, wherein the alfalfa seed is first generation progeny seed from alfalfa variety CW 104014.

8. The method of claim 6, wherein growing the plant under pollinating conditions comprises crossing the plant with a second plant of a different alfalfa variety.

9. An F1 hybrid seed, or an F1 plant grown therefrom, produced by the method of claim 8.

10. A plant of alfalfa variety CW 104014, the plant further comprising a transgene, wherein a sample of seed of alfalfa variety CW 104014 has been deposited under ATCC Accession No. PTA-124567.

11. A seed produced by the plant of claim 10.

12. Pollen or an ovule produced by the plant of claim 11.

13. The plant of claim 10, wherein the transgene confers a trait selected from the group consisting of reduced lignin content, herbicide tolerance, disease resistance, insect resistance, nematode resistance, and pest resistance.

14. A method for producing alfalfa seed, the method comprising: (a) growing plants from the seed of claim 11 under pollinating conditions; and (b) harvesting seed produced by the plants grown in step (a).

15. A method of introducing a desired trait into alfalfa variety CW 104014, the method comprising:
 (a) crossing the plant of claim 2 with plant of another alfalfa line that comprise a desired trait to produce F1 progeny plants;
 (b) selecting F1 progeny plants that have the desired trait;
 (c) crossing the selected F1 progeny plants with alfalfa variety CW 104014 plants to produce backcross progeny plants;
 (d) selecting for backcross progeny plants that comprise the desired trait and all the physiological and morphological characteristics of alfalfa variety CW 104014; and
 (e) performing steps (c) and (d) one or more times in succession to produce the selected or higher backcross progeny plants that comprise the desired trait and all of the physiological and morphological characteristics of alfalfa variety CW 104014.

16. A method for producing progeny seed, the method comprising: (a) growing the plant of claim 10 under pollinating conditions; and (b) harvesting progeny seed produced by the plant grown in step (a).

17. A progeny seed, or a progeny plant grown therefrom, produced by the method of claim 16, wherein the progeny seed is first generation progeny seed of the plant.

18. The method of claim 16, wherein growing the plant under pollinating conditions comprises crossing the plant with a second plant of a different alfalfa variety.

19. An F1 hybrid seed, or an F1 plant grown therefrom, produced by the method of claim 18.

* * * * *